(12) United States Patent  (10) Patent No.: US 9,283,114 B2
Johnson et al.  (45) Date of Patent: Mar. 15, 2016

(54) SYSTEMS AND METHODS FOR PRIMING A MICROFLUIDIC CHAMBER

(71) Applicant: ALCON RESEARCH, LTD., Fort Worth, TX (US)

(72) Inventors: Andrew David Johnson, Tustin, CA (US); Nicholas Max Gunn, Newport Beach, CA (US)

(73) Assignee: Novartis AG, Basel (CH)

( * ) Notice: Subject to any disclaimer, the term of this patent is extended or adjusted under 35 U.S.C. 154(b) by 348 days.

(21) Appl. No.: 13/975,316

(22) Filed: Aug. 24, 2013

(65) Prior Publication Data

US 2015/0057593 A1  Feb. 26, 2015

(51) Int. Cl.
*A61M 5/00* (2006.01)
*A61F 9/007* (2006.01)

(52) U.S. Cl.
CPC ....... *A61F 9/00781* (2013.01); *A61F 2240/001* (2013.01); *Y10T 29/49826* (2015.01)

(58) Field of Classification Search
CPC . A61F 9/00781; A61F 9/007; A61F 9/00761; A61F 9/0017; A61M 27/002; A61M 2210/0612; A61B 5/0084; F16K 99/0026
USPC .......................................................... 604/8, 9
See application file for complete search history.

(56) References Cited

U.S. PATENT DOCUMENTS

| | | | |
|---|---|---|---|
| 6,056,269 A | 5/2000 | Johnson et al. | |
| 6,579,235 B1 | 6/2003 | Abita et al. | |
| 7,544,176 B2 * | 6/2009 | Rodgers | A61F 9/00781 210/321.75 |
| 2002/0013545 A1 | 1/2002 | Soltanpour et al. | |
| 2002/0087111 A1 | 7/2002 | Ethier et al. | |
| 2002/0156413 A1 | 10/2002 | Williams et al. | |
| 2002/0165478 A1 | 11/2002 | Gharib et al. | |
| 2002/0169468 A1 | 11/2002 | Brown | |
| 2003/0234376 A1 | 12/2003 | Cabuz et al. | |
| 2004/0073156 A1 | 4/2004 | Brown | |
| 2004/0228734 A1 | 11/2004 | Jeon et al. | |
| 2005/0067029 A1 | 3/2005 | Henning et al. | |
| 2005/0273033 A1 | 12/2005 | Grahn et al. | |
| 2007/0243111 A1 | 10/2007 | Momose | |
| 2009/0196903 A1 | 8/2009 | Kliman | |
| 2010/0042209 A1 | 2/2010 | Guarnieri | |
| 2010/0249691 A1 | 9/2010 | Van Der Mooren et al. | |
| 2011/0071454 A1 | 3/2011 | Dos Santos et al. | |
| 2011/0082385 A1 | 4/2011 | Diaz et al. | |
| 2011/0144617 A1 | 6/2011 | Meng et al. | |
| 2011/0203700 A1 * | 8/2011 | Scholten | B01L 3/502715 141/2 |
| 2011/0282328 A1 | 11/2011 | Ambati et al. | |

(Continued)

OTHER PUBLICATIONS

International Searching Authority, International Search Report, PCT/US2014/039582, Oct. 22, 2014, 3 pages.

(Continued)

*Primary Examiner* — Philip R Wiest
(74) *Attorney, Agent, or Firm* — Kenneth D. Bassinger (57) ABSTRACT

An intraocular device for implantation in an eye of a patient is provided. The intraocular device includes an inlet tube, an outlet tube, and a microfluidic chamber. The microfluidic chamber includes a chamber inlet coupled to the inlet tube, a chamber outlet coupled to the outlet tube, and one or more fluidic barriers. Each fluidic barrier is configured such that, as a fluid is injected into the microfluidic chamber, a front of the fluid coincides with the fluidic barrier before any of the fluid passes beyond the fluidic barrier. Associated methods are also disclosed herein.

12 Claims, 6 Drawing Sheets

(56) References Cited

U.S. PATENT DOCUMENTS

| | | |
|---|---|---|
| 2012/0039770 A1 | 2/2012 | Namkoong et al. |
| 2012/0302861 A1 | 11/2012 | Marshall et al. |
| 2012/0316492 A1 | 12/2012 | Chappel |
| 2013/0000765 A1 | 1/2013 | Fernandes et al. |
| 2013/0150774 A1 | 6/2013 | Field et al. |
| 2013/0150775 A1 | 6/2013 | Dos Santos et al. |
| 2013/0150777 A1 | 6/2013 | Boehm et al. |
| 2013/0211312 A1 | 8/2013 | Gelvin |
| 2013/0317413 A1 | 11/2013 | Field et al. |

OTHER PUBLICATIONS

International Searching Authority, Written Opinion, PCT/US2014/039582, Oct. 22, 2014, 4 pages.

* cited by examiner

SYSTEMS AND METHODS FOR PRIMING A MICROFLUIDIC CHAMBER

BACKGROUND

The present disclosure relates generally to purging a gas from a microfluidic chamber. An example of such a microfluidic chamber may be presented by pressure measurement systems for use in ophthalmic treatments.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

Figure 1:
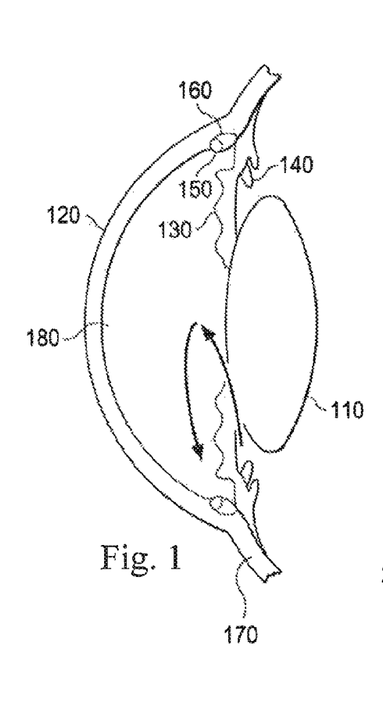
FIG. 1 is a cross-sectional view of the front portion of an eye.

FIG. 1 is a diagram of the front portion of an eye 100 that helps to explain the processes of glaucoma. In FIG. 1, representations of the lens 110, cornea 120, iris 130, ciliary body 140, trabecular meshwork 150, Schlemm's canal 160, and the edges of the sclera 170 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber 180. The edge of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The sclera 170, the white of the eye, connects to the cornea 120, forming the outer, structural layer of the eye. The two arrows in the anterior segment of FIG. 1 show the flow of aqueous humor from the ciliary bodies 140, over the lens 110, over the iris 130, through the trabecular meshwork 150, and into Schlemm's canal 160 and out its collector channels.

As part of a method for treating glaucoma, a doctor may implant a device in a patient's eye. The device may monitor the pressure in a patient's eye and facilitate control of that pressure by allowing excess aqueous humor to flow from the anterior chamber of the eye to a drainage site, relieving pressure in the eye and thus lowering IOP. To exert appropriate control, an accurate measurement of the pressure about the patient's eye may be made. In order to accurately measure pressure, one or more chambers may require priming. However, the priming of chambers of the size required for implantation into a patient's eye has not been entirely satisfactory.

The system and methods disclosed herein overcome one or more of the deficiencies of the prior art.

SUMMARY

In one exemplary aspect, the present disclosure is directed to an intraocular device for implantation in an eye of a patient. The intraocular device includes an inlet tube and an outlet tube coupled to a chamber inlet and a chamber outlet, respectively, of a microfluidic chamber. The chamber includes one or more fluidic barriers configured such that when a fluid is injected into the chamber, a front of the fluid coincides with each of the one or more fluidic barriers before any of the fluid passes beyond the fluidic barrier.

In yet another exemplary aspect, the present disclosure is directed to a method of forming a microfluidic chamber for use in an intraocular device. The method may include steps of providing a substrate, forming a bottom surface within the substrate, and forming a chamber inlet and a chamber outlet with both the chamber inlet and the chamber outlet in communication with the bottom surface. The method may further include fixing an additional substrate to the substrate. The additional substrate may have at least one fluidic barrier formed thereon such that when a fluid enters the chamber, a front of the fluid coincides with the fluidic barrier before passing beyond the at least one fluidic barrier.

In another exemplary aspect, the present disclosure is directed to a method of priming a chamber in an intraocular device. The method may include steps of coupling a liquid source to an inlet of a chamber in the intraocular device, in which the chamber including at least one barrier that provides resistance to a liquid, and injecting a first portion of the liquid through the inlet into the chamber, such that a front of the liquid coincides with the at least one barrier. The method may further include continuing to inject the liquid such that the liquid passes the at least one barrier and exits the chamber through an outlet thereof.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to a system and method for ensuring gas bubbles are fully purged from a microfluidic chamber by guiding the liquid or fluid during the priming of the chamber. The chamber may be used in connection with a pressure sensor in an intraocular device, such as a glaucoma drainage device (GDD). GDDs are used to alleviate excess pressure caused by aqueous humor accumulation in a patient's eye. A gas bubble may adversely affect the measurements made by a pressure sensor in the GDD.

The intraocular device may include an inlet and an outlet leading to and from the chamber. The chamber includes at least one fluidic barrier that inhibits the flow of a liquid beyond the barrier, such that a front of the liquid coincides with the full length of the barrier before any of the liquid passes beyond the barrier. In this manner, the liquid may flow through the chamber in a way that decreases or eliminates the formation of gas bubbles within the chamber. The systems and methods disclosed herein may thereby enable more accurate measurements in the chamber by reducing the likelihood of air bubbles, resulting in better treatment planning, potentially providing more effective treatment and greater customer satisfaction.

Figure 2:
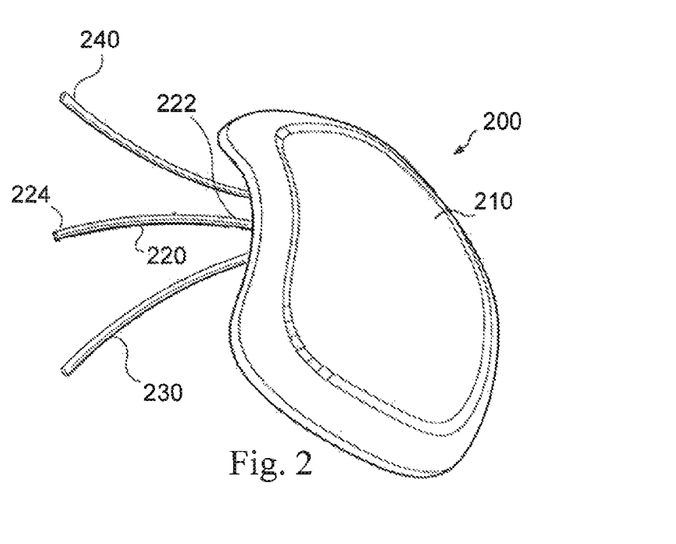
FIG. 2 is a perspective view of an intraocular implant that carries a microfluidic chamber

FIG. 2 is a view of an intraocular implant or device 200 such as may be used in the monitoring and treatment of a patient's eye. As depicted, the intraocular device 200 is a GDD. The intraocular device 200 includes a body referred to herein as a plate 210 with a drainage tube 220 that extends from the plate 210. The drainage tube 220 includes a proximal end portion 222 that couples the tube to one or more structures internal to the plate 210. A distal end portion 224 of the drainage tube 220 may be coupled to the eye of a patient to allow for the monitoring of pressure and/or the drainage of fluid. As depicted, the intraocular device 200 includes two additional tubes: an inlet tube 230 and an outlet tube 240, which may be ligated prior to implantation. The inlet tube 230 and outlet tube 240 may provide access to a chamber on the plate 210 that forms part of a passive valve system. This chamber will be discussed in greater detail below.

Figure 3:
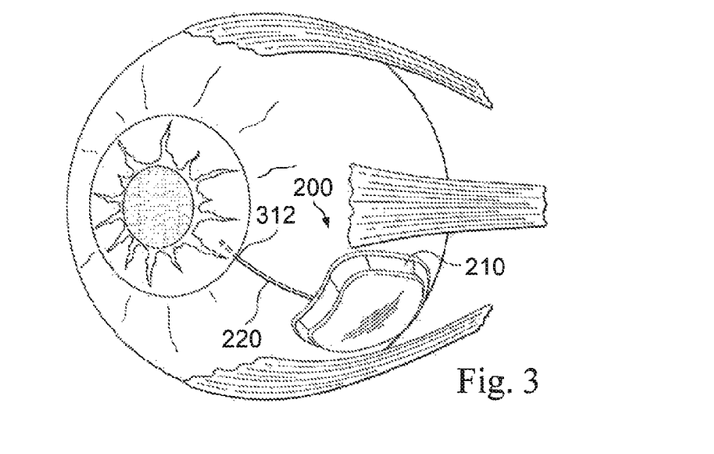
FIG. 3 is a perspective view of an intraocular implant as situated proximate an eye according to an exemplary aspect of the present disclosure.

FIG. 3 is a view of an eye of a patient whose IOP is being monitored and/or who is receiving treatment with the intraocular device 200. The plate 210 may include or be arranged to carry various components of an IOP control system (not shown). In some embodiments, such components include a power source, a processor, a memory, a data transmission module, and a flow control mechanism (i.e. valve system). It may also carry one or more pressure sensor systems.

The plate 210 is configured to fit at least partially within the subconjunctival space and is sized within a range between about 15 mm×12 mm to about 30 mm×15 mm and has a thickness less than about 2 mm thick, preferably less than about 1 mm thick. The plate 210 may be formed to the radius of the eye globe (about 0.5 inches). It may be rigid and preformed with a curvature suitable to substantially conform to the globe or it may be flexible and can flex to conform to the globe. Some embodiments are small enough that conforming to the globe provides little benefit in comfort or implantation technique. The above dimensions are exemplary only, and other sizes and arrangements are contemplated herein.

In some embodiments, the drainage tube 220 extends from an anterior side of the plate 210 and is sized and arranged to extend into the anterior chamber of the eye through a surgically formed opening 312 in the sclera. The drainage tube 220 may be used to measure pressure in addition to facilitating drainage. The drainage tube 220 includes a first open end that may be disposed at a location where pressure measurements may be desired, and at least one lumen that extends to a second open end that may be disposed within or connected to the plate 210.

Prior to placement around a patient's eye as depicted in FIG. 3, a chamber within the plate 210 may be primed by the injection of liquid that displaces a gas from the chamber. The liquid may be injected through the inlet tube 230 until some liquid may exit through the outlet tube 240. After the air is satisfactorily purged from the chamber, one or more tubes may be ligated as discussed above, and the intraocular device 200 is implanted.

Figure 4A:
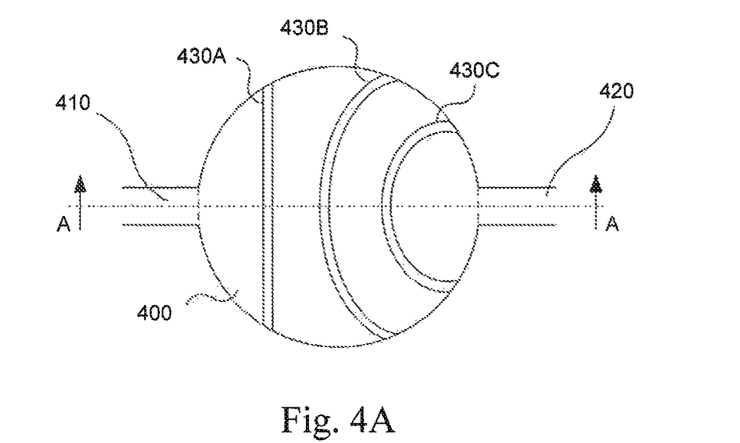
FIG. 4A is a top view of a microfluidic chamber as may be used in the intraocular implant according to an exemplary aspect of the present disclosure.

FIG. 4A is a top-view view of a microfluidic chamber 400 such as may be present in the intraocular implant 200 of FIG. 2. The chamber 400 includes a chamber inlet 410 disposed on one side and a chamber outlet 420 disposed opposite the inlet 410. However, in some embodiments, the inlet 410 and the outlet 420 may not be disposed opposite each other with respect to the volume of the chamber 400. When the chamber 400 is primed, liquid enters through the inlet 410 and displaces air out through the outlet 420.

At times, when liquid is introduced into a microfluidic chamber the liquid may begin to exit the chamber before all the gas therein is expelled, leaving behind one or more bubbles. These bubbles may prevent desired operation of valves or other components, and may result in decreased accuracy for measurements such as pressure readings. To inhibit the formation of gas bubbles within chamber 400, chamber 400 includes one or more fluidic barriers. As depicted, chamber 400 includes three such barriers: barriers 430A, 430B, and 430C. The barriers 430A-C may be straight or curved. As depicted, barrier 430A is straight or nearly straight, while both barriers 430B and 430C are curved. In some embodiments, all the barriers may be curved. The barriers 430A-C may be symmetric about an axis running from the inlet 410 to the outlet 420, depicted as line A-A. The radii of curvature of barriers 430A-C may decrease with proximity to the outlet 420. Thus, as depicted in FIG. 4A, barrier 430C has a lower radius of curvature than barrier 430B, which has a lower radius of curvature than barrier 430A.

Figure 4B:
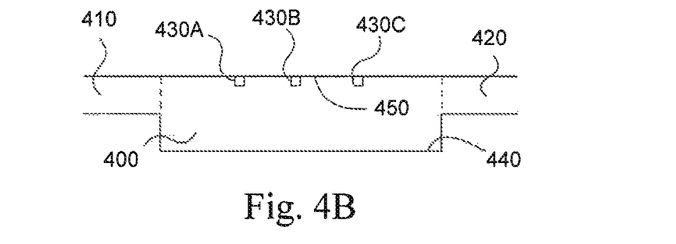
FIG. 4B is a cross-sectional view of the microfluidic chamber of FIG. 4A according to an exemplary aspect of the present disclosure.

FIG. 4B is a cross-sectional view of the microfluidic chamber of FIG. 4A as viewed along line A-A. As seen in cross-section, chamber 400 includes a bottom surface 440 and a top surface 450. In some embodiments, a distance between the bottom surface 440 and the top surface 450 within the chamber 400 may range from around 200 to around 500 microns. For example, in some embodiments the distance may be around 400 microns. As seen in the cross-section of FIG. 4B, the barriers 430A-C are structures that protrude or extend from the top surface 450 toward the bottom surface 440. Given the scale of the chamber 400, the orientation of the chamber 400 is not critical. Accordingly, the designations "top" surface 450 and "bottom" surface 440 are arbitrary and should be understood as helping to describe a relationship of one surface to the other. As depicted, bottom surface 440 is circular, but other embodiments may be elliptical or have another shape.

The protrusions of barriers 430A-C may be rectangular, triangular, trapezoidal, or curved in cross-sectional shape. The protrusions of barriers 430A-C extend into the chamber 400 by around 50 microns. The appropriate protrusion height depends on the surface tension characteristics of the priming liquid as well as the dimension of the chamber, and may range from 10 to 100 microns. Due to the microfluidic conditions within the chamber 400, as a liquid flows from the inlet 410 to the outlet 420, the front of the liquid remains in contact with both the top surface 450 and the bottom surface 440. The front of the liquid is the leading surface of the liquid as it is introduced into the chamber 400 and flows through it to the outlet 420. When the front of the liquid comes into contact with one of the barriers 430A-C, such as barrier 430A, the front of the liquid may not pass beyond the barrier until it first coincides with the full length of the barrier. Once the liquid front can no longer expand laterally along the barrier it then passes that barrier, as will be discussed in greater detail below.

Figure 4C:
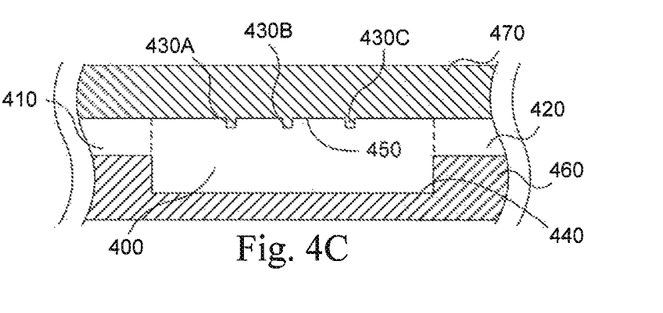
FIG. 4C is an alternative cross-sectional view of the microfluidic chamber of FIG. 4A according to an exemplary aspect of the present disclosure.

FIG. 4C is an additional, fragmentary cross-sectional view of the microfluidic chamber 400 of FIG. 4A as viewed along the line A-A. FIG. 4B may provide additional details regarding the construction or fabrication of the chamber 400. In some embodiments, the bottom portion of the chamber 400, including the bottom surface 440, is fabricated in a substrate 460, only a portion of which is shown. Embodiments of the substrate 460 may be made from a variety of materials including glass, silicon, polyetheretherketone (PEEK), or other material. The substrate 460 may be machined or etched to form the bottom portion of chamber 400. The substrate 460 may have many other features that are not depicted in FIG. 4C, such as additional microfluidic structures and channels, sensors, and associated controllers and circuitry.

The top surface 450 of the chamber 400 may be formed in an additional substrate 470, which may be made of the same materials as the substrate 460. Only a portion of the additional substrate 470 is depicted in FIG. 4C. The additional substrate 470 may be etched or machined to produce the protruding barriers 430A-C and top surface 450. After the formation of the bottom surface 440 and the top surface 450, the substrates 460 and 470 may be fixed together. This fixation may be provided by a bonding or adhesion process.

Some embodiments of the chamber 400 may include a different type of barrier rather than the barriers 430A-C as depicted. For example, rather than being provided by protrusions, the fluidic barriers may be slots or recesses produced by removal of material, by etching, machining, or other appropriate process, such that the top view is as depicted in FIG. 4A. In such embodiments, corresponding cross-sectional views may depict recessed barriers 430A-C, rather than protruding barriers 430A-C.

Figure 5A:
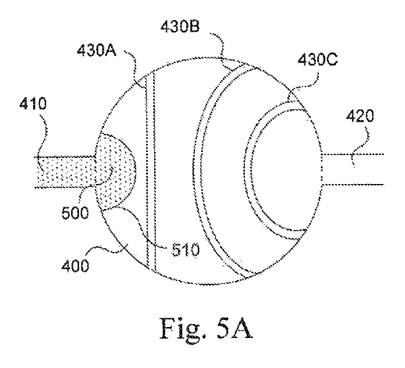
FIGS. 5A, 5B, 5C, 5D, and 5E are top views showing the microfluidic chamber of FIGS. 4A-C in various stages of priming.

FIGS. 5A, 5B, 5C, 5D, and 5E are top-view views showing the microfluidic chamber 400 of FIGS. 4A-4C in various stages of priming. Each of the FIGS. 5A-E depicts a liquid 500 as it enters through the inlet 410 and exits through the outlet 420. While any purging liquid may be used, some embodiments employ a saline solution. As depicted in FIG. 5A, the liquid 500 has passed through the inlet 410 entering into the chamber 400. As the volume of liquid 500 within the chamber 400 increases, a front 510 of the liquid progresses toward barrier 430A.

Figure 5B:
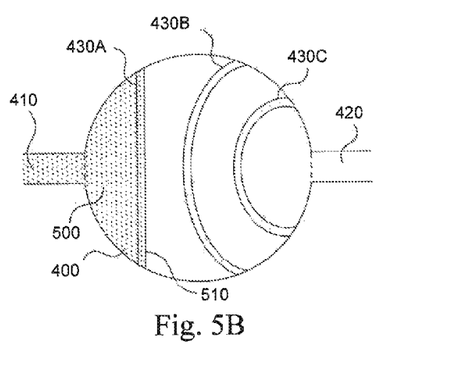

When a portion of the front 510 contacts the barrier 430A, the far side of the barrier 430A may inhibit the progress of the front 510. The resistance to the liquid front 510 provided by the barrier 430A directs an additional volume of liquid 500 laterally along the barrier 430A as it is injected until the front 510 coincides with the barrier 430A, as depicted in FIG. 5B. The resistance provided by the barrier 430A may not be overcome until all the space between the inlet 410 and the barrier 430A is filled.

Figure 5C:
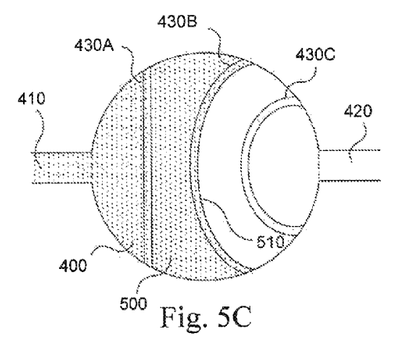
Figure 5D:
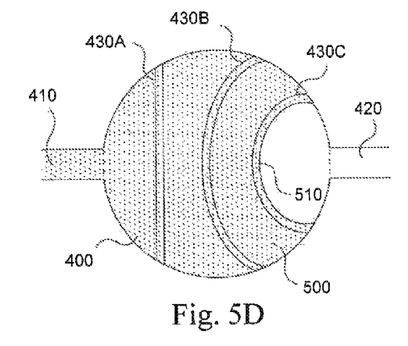
Figure 5E:
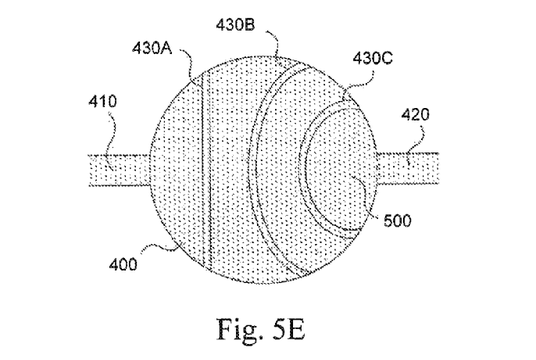

When the front 510 and the barrier 430A coincide, additional liquid 500 causes the front 510 to flow beyond the barrier 430A. This additional liquid 500 begins to fill the space defined between the barrier 430A and the barrier 430B. When the front 510 encounters the barrier 430B, the barrier 430B provides resistance to the front 510 such that additional liquid is directed along the barrier 430B as more liquid is injected. When the front 510 coincides with the barrier 430B, as depicted in FIG. 5C, additional liquid 500 may overcome the resistance and pass beyond the barrier 430B. Similarly, the space between the barrier 430C and the barrier 430B may fill (as depicted in FIG. 5D) before any liquid 500 passes beyond the barrier 430C. When a sufficient volume of liquid 500 is injected through the inlet 410 into the chamber 400, the liquid 500 passes beyond each of the barrier 430A-C and exits through the outlet 420. Thus, as liquid 500 is continuously injected into the inlet 410, the barrier 430A may cause the volume defined between it and the inlet 410 to fill, and then barrier 430B may cause the volume defined between it and the barrier 430A to fill, before any of the liquid 500 exits through the outlet 420 as depicted in FIG. 5E.

Some embodiments of the chamber 400 include more or fewer than the three barriers 430A-C depicted in FIGS. 4A-C and 5A-D. In such embodiments, the passage of the liquid 500 from the inlet 410 to the outlet 420 may be substantially as described above. Additionally, in embodiments in which the barriers 430A-C are recesses, rather than protrusion, a similar process may occur. However, in such recessed barrier embodiments the resistance to the front 510 may be provided at a lip present at a near side of each barrier. In general, the barriers 430A-C guide the front 510 of the liquid 500 to the sides of the chamber 400 to prevent the formation of bubbles along the sides thereof.

Figure 6A:
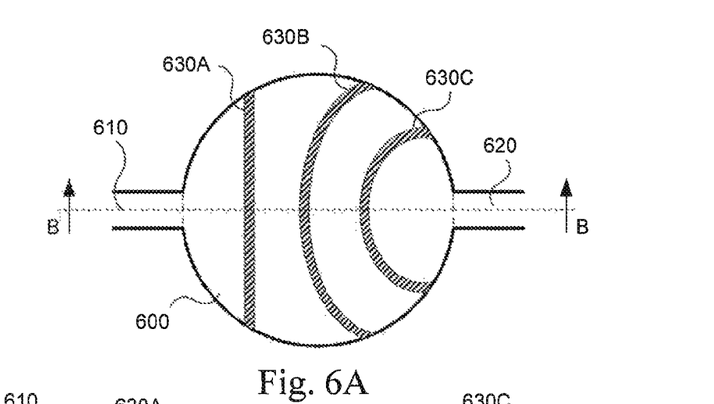
FIG. 6A is a top view of a microfluidic chamber such as may be used in the intraocular implant according to an exemplary aspect of the present disclosure.

FIG. 6A is a top-view view of a microfluidic chamber 600 as may be used in the intraocular implant 200. The microfluidic chamber 600 shares many features of the chamber 400 described above. Thus, an inlet 610 is configured to permit fluid to enter into the microfluidic chamber 600, while an outlet 620 allows fluid to exit the chamber 600. To help prevent the formation of bubbles along the sides of the chamber 600, a plurality of microfluidic barriers may be present therein. As depicted, three barriers are present, including barriers 630A, 630B, and 630C. Some embodiments of the chamber 600 may include more or fewer barriers than depicted in FIG. 6A. Unlike the barriers 430A-C, barriers 630A-C may not protrude from or recess into a top surface of chamber 600. Instead, a surface treatment may be applied to the area of barriers 630A-C to alter their hydrophobicity relative to the rest of the top surface of chamber 600. For example, barriers 630A-C may be hydrophobic areas relative to the rest of the top surface of the chamber 600. As in the chamber 400, embodiments of the chamber 600 may include barriers 430A-C having significantly different radii of curvature.

Figure 6B:
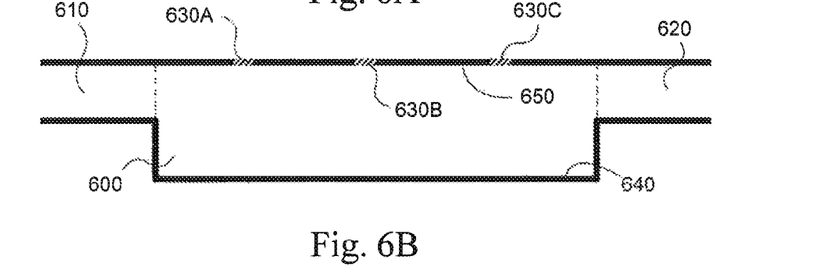
FIG. 6B is a cross-sectional view of the microfluidic chamber of FIG. 6A according to an exemplary aspect of the present disclosure.

FIG. 6B is a cross-sectional view of the microfluidic chamber 600 of FIG. 6A as seen along line B-B. This perspective may be helpful in understanding how a top surface 650 of the chamber 600 provides the barriers 630A-C. A lower substrate may be shaped to form the bottom surface 640, while an upper substrate may be shaped to form the top surface 650. In general, the bottom surface 640 and the top surface 650 may be hydrophilic surfaces. In such embodiments, the barriers 630A-C may be made hydrophobic by chemical or mechanical treatment applied to areas the top surface 650 corresponding to the barriers. The operation of the chamber 600 may be similar to the chamber 400 as depicted in FIGS. 5A-E. Thus, the progress of a liquid front moving from the inlet 610 to the outlet 620 may encounter resistance where the top surface 650 changes from a hydrophilic surface to the relatively hydrophobic surface of one of barriers 630A-C. This resistance may direct the liquid laterally to the sides of the chamber 600, causing an area behind the barrier to fill with liquid, before the front of the liquid passes the barrier.

Figure 7A:
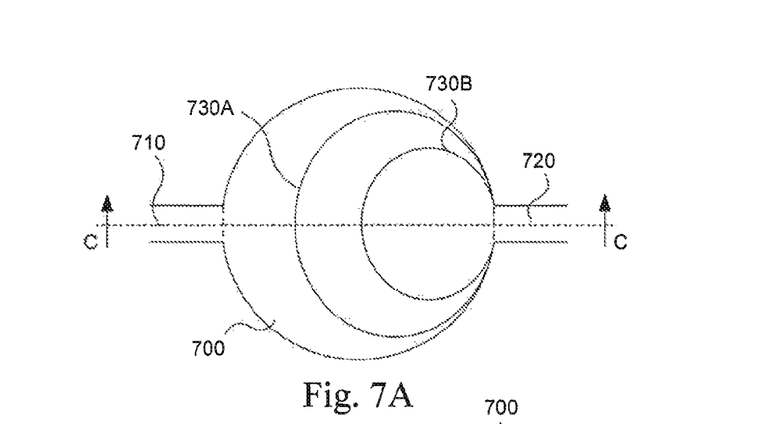
FIG. 7A is a top view of a microfluidic chamber such as may be used in the intraocular implant according to an exemplary aspect of the present disclosure.

FIG. 7A is a top-view view of a microfluidic chamber 700 such as may be used in an intraocular implant. Like chambers 400 and 600, the chamber 700 may guide a fluid in such a way as to prevent the formation of bubbles along the sides of the chamber. Chamber 700 includes an inlet 710 and an outlet 720 that allow a liquid to enter and exit the chamber. Also like chambers 400 and 600 discussed above, chamber 700 includes one or more barriers that may guide injected fluid laterally toward the sides and along the barrier before the fluid front moves beyond the barrier. Chamber 700 includes a plurality of shelf-type barriers 730A and 730B. As depicted, each of the barriers 730A and 730B is curved, however in some embodiments one or more may be straight as seen from above. The barriers 730A-B may be better understood by reference to FIG. 7B.

Figure 7B:
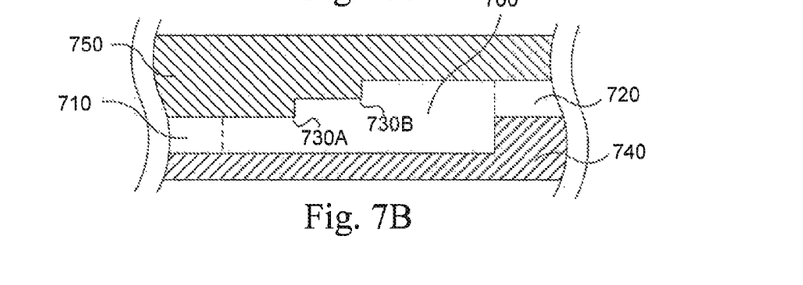
FIG. 7B is a cross-sectional view of the microfluidic chamber of FIG. 7A according to an exemplary aspect of the present disclosure.

FIG. 7B is a fragmentary, cross-sectional view of the microfluidic chamber 700 of FIG. 7A as seen along a line C-C of FIG. 7A. As depicted in FIG. 7B, the microfluidic chamber 700 includes an inlet 710 at a first level, the first level being defined by a height of the chamber 700. The barrier 730A is formed by a change in the height of the chamber 700. In some embodiments, like that depicted, the change in height is an increase in the height. Thus, barrier 730A may be provided by a change in height within chamber 700. This change may be from about 10 microns to about 100 microns. In some embodiments, a change in height of the chamber 700 that is about 50 microns may be used to form barrier 730A. An additional change of height within the chamber 700 may provide barrier 730B. The changes in height may be produced by machining or etching a bottom substrate 740 and a top substrate 750 (a portion of both being depicted) and then fixing them together in alignment. Embodiments of the chamber 700 may include more or fewer barriers than depicted. In some embodiments, the inlet 710 and the outlet 720 may be coplanar. The operation of the chamber 700 may be better understood by reference to FIGS. 8A-H.

Figure 8A:
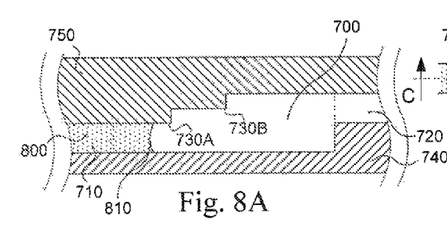
FIGS. 8A and 8B, 8C and 8D, 8E and 8F, and 8G and 8H are pairs of cross-sectional views and top views showing the microfluidic chamber of FIGS. 7A and 7B in various stages of priming according to an exemplary aspect of the present disclosure.
Figure 8B:
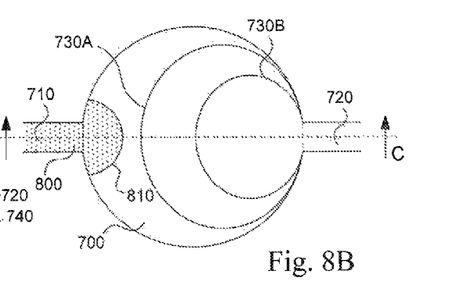
Figure 8C:
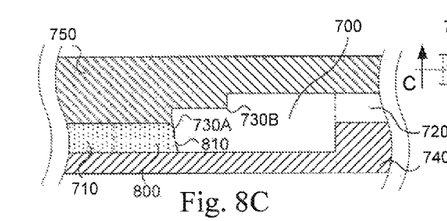
Figure 8D:
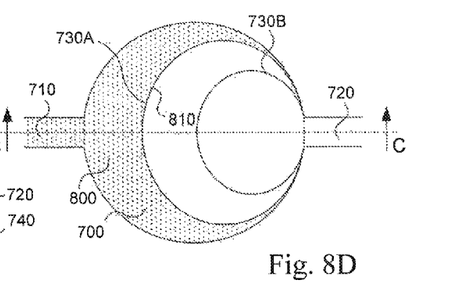

FIGS. 8A and 8B, 8C and 8D, 8E and 8F, and 8G and 8H are pairs of fragmentary cross-sectional and top-view views showing the microfluidic chamber 700 in various stages of priming with a liquid 800. In FIGS. 8A and 8B, the liquid 800 is injected through the inlet 710 and enters into the chamber 700. A front 810 of the liquid 800 is seen approaching the barrier 730A. When part of the front 810 comes into contact with the barrier 730A, the resistance provided by the barrier 730A may inhibit the front 810 from passing the barrier. Instead, the barrier 730A may direct the liquid 800 to the sides of the chamber 700. When the liquid front 810 coincides with the barrier 730A, as depicted in FIGS. 8C and 8D, then the resistance provided by the barrier may be overcome by the continually injected liquid 800. The front 810 may then pass beyond barrier 730A.

Figure 8E:
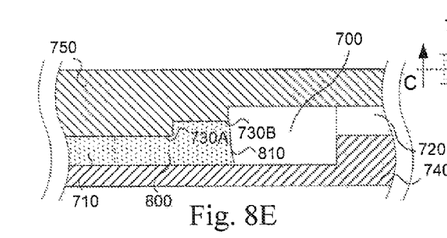
Figure 8F:
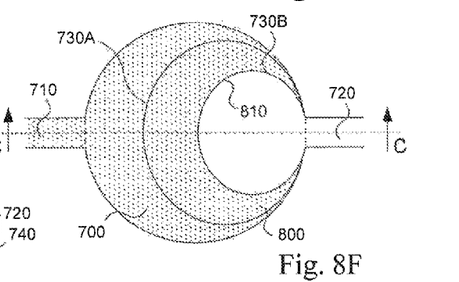
Figure 8G:
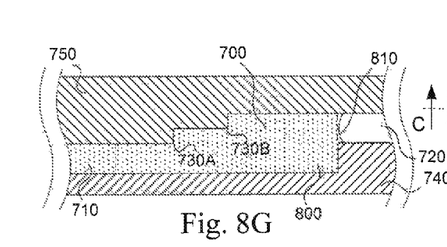
Figure 8H:
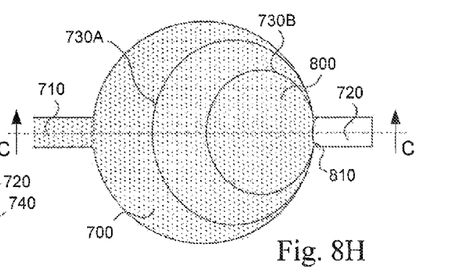

As more liquid 800 is injected through the inlet 710 into the chamber 700, a portion of the front 810 encounters resistance at the barrier 730B, such that the liquid 800 is redirected laterally until the front 810 coincides with the barrier 730B along its entire length. This is depicted in FIGS. 8E and 8F. As liquid 800 is continuously injected, the front 810 overcomes the resistance and moves beyond the barrier 730B. In embodiments having more barriers, a similar process may occur at each barrier as the volume of liquid 800 injected into the chamber 700 increases. After a sufficient volume of liquid 800 has been injected to fill the chamber 700, the front 810 moves out of the chamber 700 and through the outlet 720, as depicted in FIGS. 8G and 8H. The resistance applied by the barriers 730A and 730B to the front 810 may force liquid 800 to the sides of chamber 700 so as to remove bubbles and/or prevent their formation.

Figure 9:
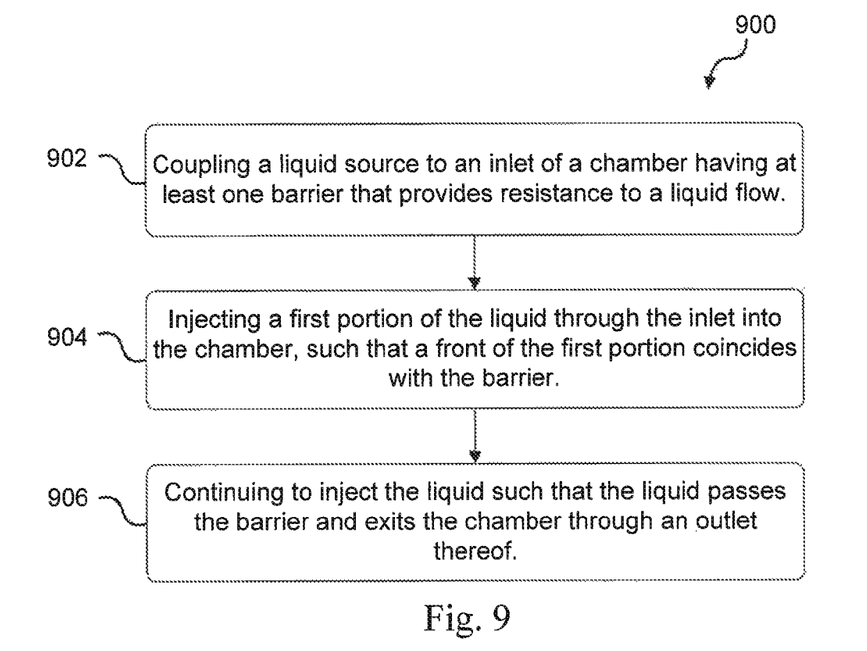
FIG. 9 is a flowchart showing a method of priming a microfluidic chamber according to an exemplary aspect of the present disclosure.

FIG. 9 is a flowchart of a method 900 of priming a microfluidic chamber according to an exemplary aspect of the present disclosure. Method 900 includes a plurality of enumerated steps, but embodiments of method 900 may further include additional steps before, in between, and after the enumerated steps. Method 900 may begin at step 902 in which a liquid source is coupled to an inlet of a chamber in an intraocular device. The chamber includes at least one barrier that provides resistance to a liquid. At step 904, a first portion of the liquid is injected through the inlet into the chamber. As the liquid is injected into the chamber, the first portion of the liquid may expand until a front of the first portion coincides with the at least one barrier. At step 906, the injection of liquid may continue such that the liquid and the front thereof passes the barrier and exits the chamber through an outlet.

In order to better describe the method 900, reference will now be made to chamber 700 as depicted in FIGS. 7A-B and 8A-G. Method 900 may also be performed with other chambers, such as chamber 400 and chamber 600 as described above. At step 902, prior to implantation next to a patient's eye, a doctor or technician may couple a liquid source such as a syringe to a tube coupled to the inlet 710. The doctor may use the syringe to inject the liquid 800 into the inlet 710 and thereby into the chamber 700. At step 904, while injecting the liquid 800, the doctor may inject a first portion of the liquid through the inlet 710 until the front 810 of liquid 800 coincides with the barrier 730A. As the doctor continues to inject the liquid 800, the front 810 passes beyond the barrier 730A and begins to fill a volume that may be defined between the barrier 730A and the barrier 730B. Once the front 810 coincides with the barrier 730B, as the doctor continues to inject the liquid 800 the front 810 moves beyond the barrier 730B. At step 906, when a sufficient amount of liquid 800 is injected through the inlet 710 to fill the chamber 700, as the doctor continues to inject the liquid 800 the front 810 exits the chamber and moves through the outlet 720.

In this manner, method 900 may prevent or decrease the incidence of bubble formation and trapping within the chamber 700. As the liquid 800 continuously enters the chamber 700, it fills a first discrete portion thereof defined by the barriers present within the chamber before it fills a second discrete portion, and so on as the case may be, and then exits the chamber. As liquid 800 exits the chamber 700 through the outlet 720, it may pass through an outlet tube coupled to the outlet of the chamber. The doctor or technician may understand from the liquid 800 exiting the outlet tube that the chamber 700 is primed, and thereafter may ligate the inlet tube, the outlet tube, or both. In some instances, neither the inlet tube nor the outlet tube is ligated.

Figure 10:
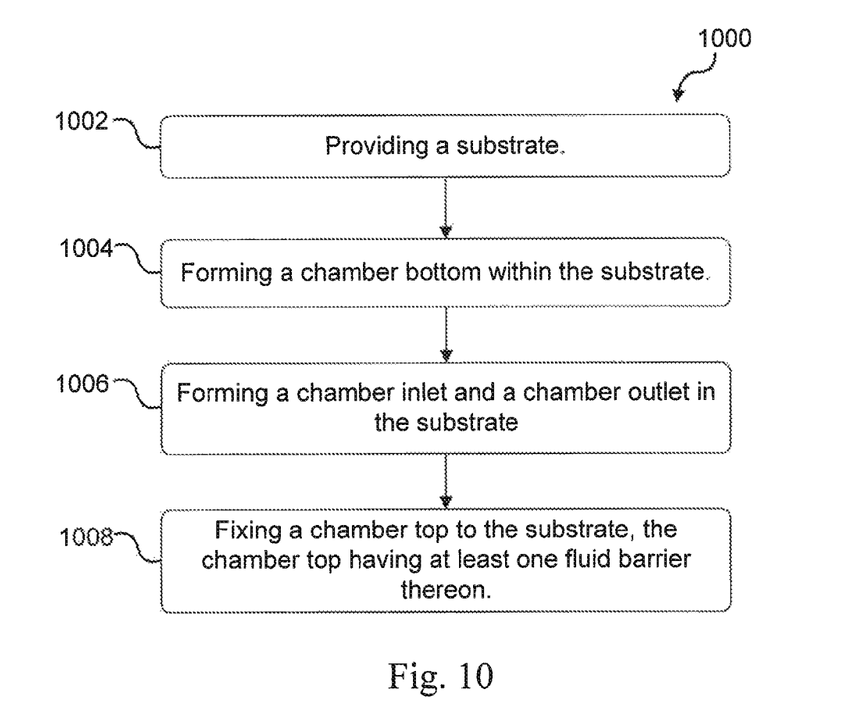
FIG. 10 is a flowchart showing a method of forming a microfluidic chamber according to an exemplary aspect of the present disclosure.

FIG. 10 is a flowchart of a method 1000 of forming a microfluidic chamber according to many embodiments of the disclosure. In other words, the method 1000 may be performed to form the microfluidic chambers 400, 600, and/or 700 as described and depicted herein. Embodiments of the method 1000 may include additional steps before, in between, and/or after the enumerated steps of the method. As depicted in FIG. 10, the method 1000 may begin at step 1002 in which a substrate is provided. A bottom surface is formed within the substrate, at step 1004. Additionally, a chamber inlet and a chamber outlet are formed in the substrate, at step 1006. At step 1008, an additional substrate having at least one fluidic barrier thereon is fixed to the substrate.

As discussed above, the method 1000 may be performed to form embodiments of the microfluidic chambers 400, 600, and/or 700. In order to better describe the method 1000, reference will be made to the microfluidic chamber 400 as depicted in FIGS. 4A-C and described in corresponding sections above. In FIG. 4C, a substrate 460 is depicted after some patterning. At step 1002, this substrate 460 may be provided as a blank, planar substrate prepared for patterning by chemical and/or mechanical processing. As discussed above, the substrate 460 may be a plastic substrate, such as PEEK, or a ceramic substrate, such as glass or silicon.

At step 1004, the substrate 460 may be patterned by an etching process to form the bottom surface 440 of the chamber. At step 1006, either by the same patterning process, or an earlier or later process, the inlet 410 and the outlet 420 are formed. An additional substrate 470 is also provided. The additional substrate 470 may be patterned by an appropriate process to form one or more fluidic barriers. At step 1008, the substrate 460 and the additional substrate 470 are then fixed together by a bonding or adhesive process, or other such suitable process. In order to incorporate the chamber 400 into an intraocular device, an inlet tube may be coupled to the inlet 410 and an outlet tube may be coupled to the outlet 420.

In some embodiments of the method 1000, the bottom surface and the inlet and outlet may be formed such that they may be removed after the additional substrate is fixed to the substrate. For example, using semiconductor processing technology, such as those used in complementary metal-oxide-silicon (CMOS) and microelectromechanical system (MEMS) fabrication, the bottom surface, inlet, and outlet may be presented when a top layer is deposited as the additional substrate 470. After the deposition of the additional substrate 470, material defining the bottom surface, inlet, and outlet may be removed by an etchant to form the corresponding structures.

In forming the one or more fluidic barriers on the additional substrate, any of the barriers described above, such as protruding barriers, recessed barriers, hydrophobicity-based barriers, or shelf-type barriers, may be used in various embodiments. In some embodiments, combinations of these and other types of fluidic barriers may be used. Additionally, some features described above as being formed in the additional substrate may be formed in the bottom substrate, and similarly some features described above as being formed in the substrate may be formed in the additional substrate. For example, a microfluidic chamber may be formed in which the inlet and the outlet are formed in the substrate that is processed to provide the top surface of the chamber. In other embodiments, portions of the inlet and the outlet may be formed in both the additional substrate and the bottom substrate. The arrangement of the fluidic barriers may also vary in different embodiments. For example, some or all of the barriers may be formed on the bottom surface. In such embodiments, the process of priming the chamber formed in such a manner may be substantially similar as the processes described above and depicted in FIGS. 5A-E and 8A-G.

The systems and methods disclosed herein may be used to provide better performance for intraocular devices, such as increased accuracy in pressure measurements. This may be done by guiding a front of an injected liquid toward the sides of a chamber before the liquid progresses closer to the chamber exit. This may result in more effective treatment and more accurate data, thereby improving the overall clinical result.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraocular device for implantation in an eye of a patient, comprising:
   an inlet tube;
   an outlet tube;
   a microfluidic chamber comprising:
      a chamber inlet coupled to the inlet tube;
      a chamber outlet coupled to the outlet tube; and
      three fluidic barriers configured such that a front of a fluid injected into the microfluidic chamber coincides with each fluidic barrier before the fluid passes beyond the fluidic barrier; wherein the first fluidic barrier comprises a linear wall portion, the second fluidic barrier comprises an arcuate wall portion with a first radius of curvature, and the third fluidic barrier comprises an arcuate wall portion with a second radius of curvature.

2. The intraocular device of claim 1, wherein at least one of the three fluidic barriers is positioned on a surface of the microfluidic chamber.

3. The intraocular device of claim 1, wherein at least one of the three fluidic barriers comprises a protrusion protruding from a surface of the microfluidic chamber.

4. The intraocular device of claim 3, wherein a side of the protrusion closest to the chamber outlet forms an angle of at least 90 degrees with respect to the surface of the microfluidic chamber.

5. The intraocular device of claim 1, wherein the first radius of curvature is greater than the second radius of curvature.

6. The intraocular device of claim 1, wherein a height of the chamber is between 200 and 500 microns.

7. The intraocular device of claim 1, wherein a height of at least one of the three fluidic barriers is between 10 and 100 microns.

8. The intraocular device of claim 1, wherein at least one of the three fluidic barriers is provided by a hydrophobic surface.

9. The intraocular device of claim 1, wherein the microfluidic chamber is cylindrical.

10. The intraocular device of claim 1, wherein at least one of the three fluidic barriers comprises a fluidic barrier step.

11. The intraocular device of claim 1, wherein at least one of the three fluidic barriers has a rectangular or trapezoidal cross-section.

12. The intraocular device of claim 1, wherein the three fluidic barriers are arranged symmetrically about a line extending from the chamber inlet to the chamber outlet.

* * * * *